(12) United States Patent
Lawson et al.

(10) Patent No.: US 10,533,414 B2
(45) Date of Patent: Jan. 14, 2020

(54) APPLICATIONS OF ADVANCED ISOTOPE GEOCHEMISTRY OF HYDROCARBONS AND INERT GASES TO PETROLEUM PRODUCTION ENGINEERING

(71) Applicants: Michael Lawson, Spring, TX (US); Brian K. Peterson, Fogelsville, PA (US); Cara L. Davis, Houston, TX (US); David R. Converse, Houston, TX (US); Timothy K. Ellison, Houston, TX (US); John Eiler, Sierra Madre, CA (US)

(72) Inventors: Michael Lawson, Spring, TX (US); Brian K. Peterson, Fogelsville, PA (US); Cara L. Davis, Houston, TX (US); David R. Converse, Houston, TX (US); Timothy K. Ellison, Houston, TX (US); John Eiler, Sierra Madre, CA (US)

(*) Notice: Subject to any disclaimer, the term of this patent is extended or adjusted under 35 U.S.C. 154(b) by 282 days.

(21) Appl. No.: 14/994,577

(22) Filed: Jan. 13, 2016

(65) Prior Publication Data

US 2016/0222782 A1  Aug. 4, 2016

Related U.S. Application Data

(60) Provisional application No. 62/111,478, filed on Feb. 3, 2015.

(51) Int. Cl.
*E21B 49/08* (2006.01)
*G01V 9/00* (2006.01)
(Continued)

(52) U.S. Cl.
CPC ....... *E21B 49/088* (2013.01); *G01N 33/2841* (2013.01)

(58) Field of Classification Search
None
See application file for complete search history.

(56) References Cited

U.S. PATENT DOCUMENTS

| 5,388,456 A | 2/1995 | Kettel |
| 6,613,520 B2 | 9/2003 | Ashby |

(Continued)

FOREIGN PATENT DOCUMENTS

| WO | WO 2007/008932 | 1/2007 | |
| WO | WO 2007008932 A2 * | 1/2007 | ......... G01N 21/3504 |
| WO | WO 2013/148442 | 10/2013 | |

OTHER PUBLICATIONS

Stolper (New Insight Into the Formation and Modification of Carbonate-bearing minerals and methane gas in Geological Systems using Multiply Substituted Isotopologues).*

(Continued)

*Primary Examiner* — Herve-Louis Y Assouman

(57) ABSTRACT

A system and method is provided for enhancing hydrocarbon production. The method and system involve geochemistry analysis and include multiply substituted isotopologue and position specific isotope geochemistry for at least one hydrocarbon compound of interest associated with free gas and sorbed gas. The method and system involve using clumped isotope and position specific isotope signatures to enhance monitoring of well and stimulation performance.

11 Claims, 3 Drawing Sheets

(51) Int. Cl.
G01N 33/24 (2006.01)
G01N 33/28 (2006.01)

(56) References Cited

U.S. PATENT DOCUMENTS

| | | | |
|---|---|---|---|
| 7,124,030 B2 | 10/2006 | Ellis | |
| 7,174,254 B2 | 2/2007 | Ellis | |
| 7,529,626 B1 | 5/2009 | Ellis | |
| 8,071,295 B2 | 12/2011 | Ashby | |
| 8,316,934 B2 | 11/2012 | Pietrobon | |
| 8,476,016 B2 | 7/2013 | Ashby | |
| 8,505,375 B2 | 8/2013 | Smalley | |
| RE44,728 E | 1/2014 | Pope et al. | |
| 8,760,657 B2 | 6/2014 | Pope et al. | |
| 8,950,251 B2 | 2/2015 | Valentine | |
| 2008/0147326 A1 | 6/2008 | Ellis | |
| 2010/0326651 A1* | 12/2010 | Pietrobon | E21B 43/14 166/250.01 |
| 2011/0250582 A1 | 10/2011 | Gates et al. | |
| 2012/0134749 A1 | 5/2012 | Darrah | |
| 2013/0091925 A1* | 4/2013 | Darrah | G01V 5/06 73/23.35 |
| 2013/0103337 A1 | 4/2013 | Eiler | |
| 2013/0116126 A1 | 5/2013 | Ashby et al. | |
| 2014/0011692 A1 | 1/2014 | Ashby | |
| 2014/0138528 A1 | 5/2014 | Pope et al. | |
| 2014/0162274 A1 | 6/2014 | Kunin et al. | |
| 2014/0250999 A1 | 9/2014 | Lawson et al. | |
| 2014/0288853 A1 | 9/2014 | Dreyfus et al. | |
| 2015/0038348 A1 | 2/2015 | Ashby et al. | |

OTHER PUBLICATIONS

Dennis et al. (Geochinnica et Cosnnochinnica Acta vol. 75, Issue 22, Nov. 15, 2011, pp. 7117-7131) (Year: 2011).*
Berner, U., et al. (1988), "Maturity Related Mixing Model for Methane, Ethane and Propane, Based on Carbon Isotopes", Advances in Organic Geochemistry, vol. 13, Nos. 1-3, pp. 67-72.
Stahl, W.J., (1977), "Carbon and Nitrogen Isotopes in Hydrocarbon Research and Exploration", Chemical Geology, vol. 20, pp. 121-149.
Chung, H.M., et al., (1979), "Use of Stable Carbon Isotope Compositions of Pyrolytically Derived Methane as Maturity Indices for Carbonaceous Materials", Geochimica et Cosmochimica Acta, vol. 43, pp. 1979-1988.
James, A.T., (1990), "Correlation of Reservoired Gases Using the Carbon Isotopic Compositions of Wet Gas Components", The American Association of Petroleum Geologists Bulletin, vol. 74, No. 9, pp. 1441-1458.
Whiticar, M.J., (1996), "Stable Isotope Geochemistry of Coals, Humic Kerogens and Related Natural Gases", vol. 32, pp. 191-215.
Stolper, D.A., et al. (2014), "Formation Temperatures of Thermogenic and Biogenic Methane", Science, vol. 344, pp. 1500-1503.
Stolper, D.A., et al., (2014), "Combined 13C-D and D-D Clumping in Methane: Methods and Preliminary Results", Geochimica et Cosmochimica Acta, vol. 126, pp. 169-191.
Urey, H.C., et al., (1933), "Some Thermodynamic Properties of the H1H2, H2H2 Molecules and Compounds Containing The H2 Atom", Journal of Chemical Physics, vol. 1, pp. 137-143.
Bigeleisen, J., et al., (1947), "Calculation of Equilbrium Constants for Isotopic Exchange Reactions", The Journal of Chemical Physics, vol. 15, No. 5., pp. 261-267.
Richet, R., et al., (1977), "A Review of Hydrogen, Carbon, Nitrogen, Oxygen, Sulphur, and Chlorine Stable Isotope Fractionation Among Gaseous Molecules", Ann. Rev. Earth Planet. Sci., vol. 5, pp. 65-110.
Vidler, M., et al., (2000), "Accurate Partition Function and Thermodynamic Data for Water", Journal of Chemical Physics, vol. 113, No. 21, pp. 9766-9771.

Liu, Q., et al., (2010), "On the Proper Use of the Bigeleisen-Mayer Equation and Corrections to It in the Calculation of Isotopic Fractionation Equilibrium Constants", Geochimica et Cosmochimica Acta, vol. 74, pp. 6965-6983.
Bloino, J., et al., (2012), "General Perturbative Approach for Spectroscopy, Thermodynamics, and Kinetics: Methodological Background and Benchmark Studies", J. Chem. Theory Comput., vol. 8, pp. 1015-1036.
Truhlar, D.G., et al., (1991), "Simple Perturbation Theory Estimates of Equilibrium Constants From Force Fields", J. Chem. Phys., vol. 94 (1), pp. 357-359.
Webb, M.A., et al., (2014), "Position-Specific and Clumped Stable Isotope Studies: Comparison of The Urey and Path-Integral Approaches for Carbon Dioxide, Nitrous Oxide, Methane, and Propane", J. Phys. Chem. A, vol. 118, pp. 467-474.
Rustad, J.R., et al., (2010), "Calculation of Boron-Isotope Fractionation Between B(OH)3(aq) and B(OH)4-(aq)", Geochimica et Cosmochimica Acta, vol. 74, pp. 2843-2850.
Wang, Y., et al., (2009), "Equilibrium 2H/1H Fractionations in Organic Moldecules: I. Experimental Calibration of Ab Initio Calculations", Geochimica et Cosmochimica Acta, vol. 73, pp. 7060-7075.
Reeves, E.P., et al., (2012), "Hydrogen Isotope Exchange Between n-Alkanes and Water Under Hydrothermal Conditions", Geochimica et Cosmochimica Acta, vol. 77, pp. 582-599.
Glasstone, S., et al., (1941), "The Theory of Rate Processes", McGraw-Hill, New York, pp. 249.
Burnham, A.K., et al., (1989), "A Chemical Kinetic Model of Vitrinite Maturation and Reflectance", Geochimica et Cosmochimica Acta, vol. 53, pp. 2649-2657.
Sweeney, J. J., et al., (1990), "Evaluation of a Simple Model of Vitrinite Reflectance Based on Chemical Kinetics", The American Association of Petroleum Geologists Bulletin, vol. 74, No. 10, pp. 1559-1570.
Magoon, L.B., et al., (1994), "The Petroleum System—From Source to Trap", AAPG Memoir 60, pp. 3-24.
Rustad, J.R., et al., (2007), "Ab Initio Calculation of Isotopic Fractionation in B(OH)3(aq) and BOH4-(aq)", JACS Communications, pp. 2222-2223.
Hassanzadeh G. et al. (2012) "Petroleum System Analysis Using Geochemical Studies, Isotope and 1D Basin Modeling in Hendijan Oil Field, SW Iran", International Petroleum Technology Conference.
Hohl, D. et al. (2010) "Energy, Environment and Climate Directorate White Paper", DCO Energy, Environment and Climate Workshop, Jul. 21-22, pp. 1-38.
Lee G.H. et al. (2004) "Timing of Trap Formation in the Southwestern Margin of the Ulleung Basin, East Sea (Japan Sea) and Implications for Hydrocarbon Accumulations", Geosciences Journal, vol. 8, No. 4, pp. 369-380.
Mudford B. (1995) "Timing of Hydrocarbon Generation and Accumulation in Fault-Bounded Compartments in the Norphlet Formation, Offshore Alabama", Marine and Petroleum Geology, vol. 12, No. 5, pp. 549-558.
Stopler D.A. (2014) "New Insights Into the Formation and Modification of Carbonate-Bearing Minerals and Methane Gas in Geological Systems Using Multiply Substituted Isotopologues" Thesis for Califorina Instittue of Technology.
Wang Y. et al. (2006) "Thermal Cracking History by Laboratory Kinetic Simulation of Paleozoic Oil in Eastern Tarim Basin, NW China, Implications for the Occurrence of Residudal Oil Reservoirs", Organic Geochemistry, vol. 37, pp. 1803-1815.
Xiao X.M. et al. (2009) "Tracing of Deeply-Buried Source Rock: A Case Study of the WC9-2 Petroleum Pool in the Pearl River Mouth Basin, South China Sea" Marine and Petroleum Geology, vol. 26, pp. 1365-1378.
Torgersen et al. (1999) "Air-Xe enrichments in Elk Hills oil field gases: role of water in migration and storage", Earth and Planetary Science Letters, vol. 167, pp. 239-253.

* cited by examiner

APPLICATIONS OF ADVANCED ISOTOPE GEOCHEMISTRY OF HYDROCARBONS AND INERT GASES TO PETROLEUM PRODUCTION ENGINEERING

CROSS REFERENCE TO RELATED APPLICATIONS

This application claims the benefit of U.S. Provisional Patent Application 62/111,478 filed Feb. 3, 2015 entitled APPLICATIONS OF ADVANCED ISOTOPE GEOCHEMISTRY OF HYDROCARBONS AND INERT GASES TO PETROLEUM PRODUCTION ENGINEERING, the entirety of which is incorporated by reference herein.

FIELD OF THE INVENTION

The present disclosure relates generally to the field of geochemistry including multiply substituted isotopologue and position specific isotope geochemistry. More particularly, the present disclosure describes the application of clumped isotope and position-specific isotope signatures, alongside inert gas and other stable isotope signatures, to enhance monitoring of well and stimulation performance.

BACKGROUND

This section is intended to introduce various aspects of the art, which may be associated with exemplary embodiments of the present disclosure. This discussion is believed to assist in providing a framework to facilitate a better understanding of particular aspects of the present invention. Accordingly, it should be understood that this section should be read in this light, and not necessarily as admissions of prior art.

Hydrocarbons are generated in the subsurface from source rocks rich in organic matter. Following initial deposition, source rocks are buried and subjected to increasing temperature and pressure with increasing burial. Hydrocarbons are generated when the source rocks reach temperatures sufficient for the thermal conversion of organic material to kerogen and then to free liquid and/or gaseous hydrocarbon phases, which is a process called source rock maturation. Upon generation, the hydrocarbons may subsequently be expulsed from the source rock and migrate in the subsurface to reservoir rocks (such as sandstones or limestones) that have sufficient porosity, structure and an adequate seal that make them capable of trapping the hydrocarbon phase(s), allowing hydrocarbons to accumulate. Alternatively, hydrocarbons may migrate to a surface location (e.g., sometimes referred to as a seep). Any hydrocarbons present in the subsurface may be preserved or they may be subjected to different forms of alteration. For example, biodegradation is the process of degradation or consumption of hydrocarbons by micro-organisms. Similarly, hydrocarbons may be thermally altered by exposure to temperatures above there thermal stability. Alternatively, hydrocarbons may be oxidized or consumed in processes, such as thermochemical sulfate reduction. In addition to hydrocarbons, non-hydrocarbon compounds (e.g., carbon dioxide $CO_2$, carbon monoxide CO, nitrogen $N_2$, hydrogen sulfide $H_2S$, helium He, neon Ne, argon Ar, krypton Kr, and xenon Xe) may also be present alongside hydrocarbons in subsurface accumulations. The concentration and isotopic signature of these compounds may be inherited from contact with formation waters, from mixing and interaction with other fluids in the subsurface (e.g. hydrothermal fluids, magmatic fluids) or from processes that liberate these compounds from rocks and minerals in the subsurface. Each of these processes from generation to storage and alteration influences the geochemical signature of these hydrocarbons and associated non-hydrocarbon compounds and gives rise to combined geochemical signatures that record a history of where these compounds originated and what processes they have experienced.

Evaluating and monitoring well performance, fracking and stimulation efficiency, reservoir drainage and overall production effectiveness can be challenging. Conventional tools include production logging tests, which can be costly; pressure monitoring, which may not capture full fluid flow; and tracer addition operations, which may be ineffective for tight reservoirs. Monitoring of geochemical variations on a production time-scale (e.g., time-lapse geochemistry) can be utilized, but generally does not provide advantages to the analysis if the geochemical variation between fluids from different reservoirs is slight, or if there are few geochemical components to monitor (e.g., gas reservoirs).

There remains a need in the industry for apparatus, methods, and systems to identify and enhance hydrocarbon operations. In particular, conventional techniques do not properly distinguish and/or provide accurate quantitative estimates between the amount of hydrocarbon compounds (e.g., gas or liquid) that is adsorbed onto sediments in the subsurface and the amount of hydrocarbon compounds present as a free phase or between fracture and matrix derived fluids. Further, conventional techniques do not provide effective tools that can address questions relating to the extent of fracture penetration, identify wellbore integrity concerns, and accurately determine the production fetch area for a given producing well.

SUMMARY

According to disclosed aspects and methodologies, a system and method are provided for enhancing hydrocarbon production and recovery. The method and system include using geochemistry including multiply substituted isotopologue and position specific isotope geochemistry. Further, the present techniques involve the use of clumped isotope and position specific isotope signatures, alongside inert gas and other stable isotope signatures, such as noble gas signatures, to enhance monitoring of well and stimulation performance.

In one embodiment, a method for enhancing hydrocarbon production is provided. The method comprises: obtaining a plurality of hydrocarbon samples from a target subsurface interval; analyzing each of the plurality of hydrocarbon samples for geochemical signature comprising clumped isotope and/or position specific isotope geochemistry for at least one hydrocarbon compound of interest associated with free gas and sorbed gas; converting each of the clumped isotope and/or position specific isotope geochemistry to a sorption dependent fractionation factor for each of the plurality of hydrocarbon samples; comparing the sorption dependent fractionation factor of at least two of the plurality of hydrocarbon samples; determining whether the at least one hydrocarbon compound of interest associated with free gas and sorbed gas has originated from the target interval or from a different interval; and adjusting a recovery strategy based on the determination.

In another embodiment, a system for enhancing hydrocarbon production is described. The system includes a processor; an input device in communication with the processor and configured to receive input data associated with a subsurface formation; memory in communication with the processor, the memory having a set of instructions. The set of instructions, when executed, are configured to: obtain hydrocarbon sample data associated with a plurality of hydrocarbon samples from a target subsurface interval; analyze hydrocarbon sample data for each of the plurality of hydrocarbon samples for geochemical signature comprising clumped isotope and/or position specific isotope geochemistry for at least one hydrocarbon compound of interest associated with free gas and sorbed gas; converting each of the clumped isotope and/or position specific isotope geochemistry to a sorption dependent fractionation factor for each of the plurality of hydrocarbon samples; comparing the sorption dependent fractionation factor of at least two of the plurality of hydrocarbon samples; determining whether the at least one hydrocarbon compound of interest associated with free gas and sorbed gas has originated from the target interval or from a different interval; and adjust a recovery strategy based on the determination. The system further comprises an output device that outputs the adjusted recovery strategy.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1A:
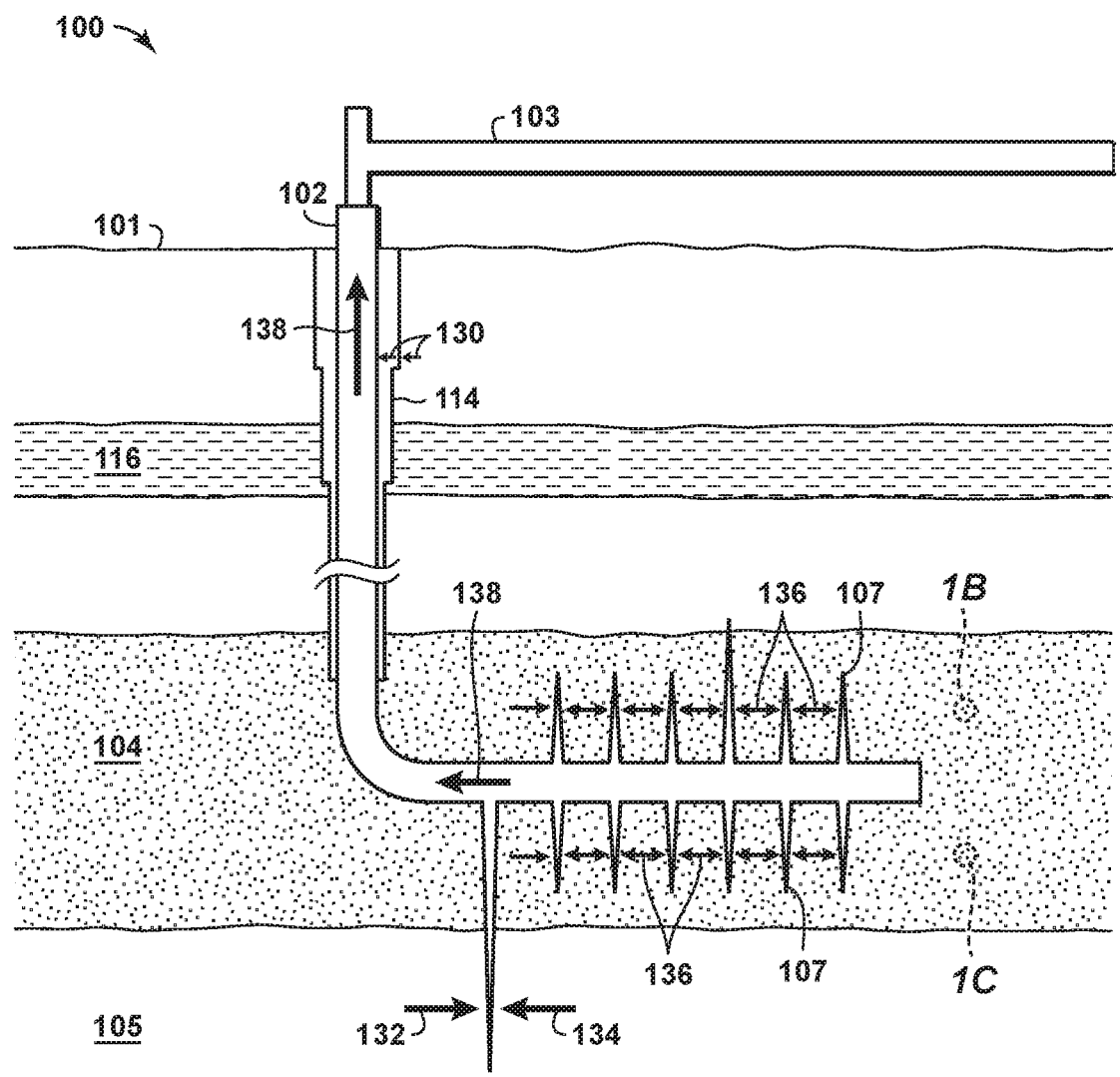
FIG. 1A is a side elevational view of the production of hydrocarbons in conventional or unconventional reservoirs.

In the following section, specific embodiments of the present techniques are described in connection with disclosed aspects and features. However, to the extent that the following description is specific to a particular aspect, technique, or a particular use, this is intended to be for exemplary purposes only. Accordingly, the invention is not limited to the disclosed aspects and techniques described below, but rather includes all alternatives, modifications, and equivalents falling within the scope of the appended claims.

Further, while for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, fewer than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

Various terms as used herein are defined below. To the extent a term used in a claim is not defined below, it should be given the definition persons in the pertinent art have given that term in the context in which it is used.

As used herein, "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprise," "comprised," "containing," "contains," "contain," "having," "has," "have," "including," "includes," and "include" are open-ended transition terms used to transition from a subject recited before the term to one or more elements recited after the term, where the element or elements listed after the transition term are not necessarily the only elements that make up the subject.

As used herein, the term "exemplary" means exclusively "serving as an example, instance, or illustration." Any embodiment described herein as exemplary is not to be construed as preferred or advantageous over other embodiments.

As used herein, the term "fracture flow" refers to the movement of reservoir fluids through natural or induced fractures or fracture networks in the rock.

As used herein, the term "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide ($H_2S$), and carbon dioxide ($CO_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicilytes, carbonates, diatomites, and other porous media.

As used herein, "hydrocarbon production" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing the wellbore to promote increased flow, well servicing, well logging, and other well and wellbore treatments.

As used herein, the term "isotope" refers to one of two or more atoms with the same atomic number but with different numbers of neutrons. Hydrocarbon molecules may contain a variety of isotopes. Hydrocarbon molecules contain both carbon and hydrogen atoms. Carbon can be present in the molecule as one of two stable isotopes: $^{12}C$, which has 6 protons and 6 neutrons (shown herein as C); and, in much lower concentrations, $^{13}C$, which has 6 protons and 7 neutrons. Similarly, hydrogen can be present in a molecule as one of two stable isotopes: H, which contains 1 proton but no neutron; and, in much lower concentrations, Deuterium (D), which has 1 proton and 1 neutron.

As used herein, "sorption dependent fractionation factor" refers to a parameter that quantitatively describes the difference in clumped isotope abundance between sorbed and free gas phases.

As used herein, the term "signatures" refers to the relative abundances, concentrations and/or ratios of various elements, isotopes, positions within a compound and isotopologues of a given species.

As used herein, the term "isotopologue" refers generally to molecules that have the same chemical composition, but have a different isotopic signature. For example, methane contains one atom of carbon and four atoms of hydrogen. Each atom in the methane structure can contain one of the two stable isotopes of that atom, and as such there are ten isotopologues of methane.

As used herein, the term "matrix flow" refers to the movement of reservoir fluids through the rock fabric.

As used herein, the term "multiply substituted isotopologue" refers generally to an isotopologue that contains at least two rare isotopes in its structure. For example, a multiply substituted methane isotopologue contain one $^{13}C$ atom and one D atom, or at least 2 D atoms in the absence of a $^{13}C$ atom.

As used herein, the term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

As used herein, the term "position specific isotope signature" refers generally to a compound that has multiple chemically or structurally distinct positions for a rare isotope to reside. For example, a position specific isotope signature in propane could refer to the position of the $^{13}C$ atom, which can be positioned either at the center of the compound or one of the end positions, or the position of the D atom, which can be attached to either a central or end position carbon.

As used herein, the term "stochastic distribution" refers generally to a system where the stable isotopes in a given population of molecules are distributed randomly among all possible isotopologues of a given species. This stochastic distribution is the reference frame from which deviations are measured and is used to provide a baseline to identify anomalies that may be associated with secondary isotope exchange processes.

As used herein, the term "spike" refers generally to the addition of a compound that has an exotic signature that does not occur naturally at such high concentrations in nature. For example, a spike could take the form of pure $^{13}CD_4$, the least abundant clumped isotopologue of methane which is not thought to be measurable at natural abundance, but could be measured if present at high concentrations.

The present techniques relate to geochemistry, and more particularly, multiply substituted isotopologue and position specific isotope geochemistry. In certain aspects, the present techniques involve the application and use of clumped isotope and position specific isotope signatures, alongside inert gas and other stable isotope signatures, to enhance monitoring of well and stimulation performance. The technology is based on the identification of these signatures to provide a unique characterization of fluids derived from different reservoir units, and/or different portions of a reservoir, and determining when and how much mixing could occur between those fluids. A unique clumped isotope and position specific signature for a reservoir fluid could be related to different sources, maturity, alteration, reservoir properties, and/or physical association within a reservoir (adsorbed versus pore space); a unique reservoir inert gas signature could be related to different proportions of hydrocarbon versus water. Integrated with other geochemical data, such information may provide more quantitative constraints on the source of hydrocarbons (gaseous and liquid) to enhance engineering solutions to ensure long term production of hydrocarbons.

According to aspects of the disclosed methodologies and techniques, the multiply substituted isotopologue or position specific isotope effects or signatures of single or numerous co-existing isotopologues of hydrocarbons can be integrated with results from other geochemical approaches that incorporate the relative or absolute concentration and isotopic signature of other hydrocarbon and non-hydrocarbon compounds (e.g., carbon dioxide ($CO_2$), carbon monoxide (CO), nitrogen ($N_2$), hydrogen sulfide ($H_2S$), helium (He), neon (Ne), argon (Ar), krypton (Kr), and xenon (Xe)) to improve monitoring of well and stimulation performance. The technology is based on the identification of these signatures to provide a unique characterization of fluids derived from different reservoir units, and/or different portions of a reservoir, and determine when and how much mixing could occur between those fluids. A unique clumped isotope and position specific signature for a reservoir fluid could be related to different sources, maturity, alteration, reservoir properties, and/or physical association within a reservoir (adsorbed versus pore space). A unique reservoir inert gas signature could be related to, amongst other things, different relative proportions of hydrocarbon versus water, contributions from the radiogenic decay of crustal minerals or magmatic fluids, modes of transport or movement of fluids (e.g. advective transport in matrix versus diffusive transport in tight rocks), physical fractionating processes such as sorption, and phase changes (e.g., liquid drop out and gas cap formation). In contrast, a unique non-hydrocarbon gas signature could arise from contributions of compounds, such as $CO_2$, $N_2$ and $H_2S$, from organic maturation or thermal alteration of minerals (temperature related), from magmatic fluids or other sources.

In one or more embodiments, the present techniques may include a method for enhancing hydrocarbon production. The method may include obtaining a plurality of hydrocarbon samples from a target subsurface interval; analyzing each of the plurality of hydrocarbon samples for geochemical signature comprising clumped isotope and/or position specific isotope geochemistry for at least one hydrocarbon compound of interest associated with free gas and sorbed gas; converting each of the clumped isotope and/or position specific isotope geochemistry to a sorption dependent fractionation factor for each of the plurality of hydrocarbon samples; comparing the sorption dependent fractionation factor of at least two of the plurality of hydrocarbon samples; determining whether the at least one hydrocarbon compound of interest associated with free gas and sorbed gas has originated from the target interval or from a different interval; and adjusting a recovery strategy based on the determination.

Techniques capable of providing this information may provide quantitative constraints on sorbed versus free gas or fracture versus matrix fluids and address problems related to fracture penetration, wellbore integrity, and production fetch area for optimal long-term hydrocarbon production strategies, to develop enhanced engineering solutions for more effective and efficient fracture penetration in conventional and unconventional reservoirs, to provide rapid identification and mitigation of well bore integrity failures or issues related to stray gas presence in aquifers and predict the production fetch area and as such more accurately quantify the estimated ultimate recovery of hydrocarbons for any given producing well.

In one or more embodiments, the present techniques may include combining multiply substituted isotopologue signatures and position specific isotope geochemistry of hydrocarbon compounds (e.g., $CH_4$, $C_2H_6$, and $C_3H_8$) and non-hydrocarbon compounds (e.g., $H_2S$, $CO_2$, $N_2$, He, Ne, Ar, Kr, and Xe) with elemental, molecular and isotopic signatures obtained from gas, oil, water and fluid inclusion samples.

The use of multiply substituted isotopologue and position specific isotope geochemistry may provide constraints on the temperature at which particular processes occur in hydrocarbon systems. When combined and integrated with traditional geochemical techniques, such as molecular (e.g., methane, ethane, carbon dioxide, nitrogen), bulk (e.g., mixtures of gases), stable isotope geochemistry (e.g., carbon, hydrogen, nitrogen, sulfur) of hydrocarbon and non-hydrocarbon gases, molecular geochemistry of oils (e.g., saturate and aromatic compounds), physical measurements (e.g., pressure, volume, and temperature (PVT)), and results from engineering tests (e.g., production logging test (PLT), or temperature logging), then these techniques provide enhancements to existing technologies to quantitatively determine the origin of hydrocarbons (e.g., produced or leaked). For example, using these technologies one can discriminate between production dominated by fracture flow and that dominated by free phase hydrocarbons or desorption of hydrocarbons from mineral or organic surfaces. In addition, contributions of hydrocarbons originating from multiple reservoir formations can be identified and quantified. For example, when artificial fractures penetrate through sealing strata and into other hydrocarbon bearing formations, or where artificial fractures intersect with natural fractures that result in contributions from other reservoirs. In addition, these technologies may be used to constrain the source of hydrocarbons within well bores when wellbore integrity is under investigation or in aquifers when present at unusually high concentrations and contamination is suspected. The technology therefore provides a mechanism to alter engineering practices and production strategies to maximize the volume and quality of hydrocarbon ultimately produced and also to mitigate any issues associated with the production of hydrocarbons if this is shown to be resulting in the leakage of hydrocarbons in the near well bore area.

Multiply substituted isotopologue geochemistry is based on the variation in the distribution of isotopes within a molecule that gives rise to molecules that are identical in their elemental composition, but that may differ in the isotopic composition of individual atoms within that molecule. These species are called isotopologues. For example, there are three isotopologues of nitrogen (e.g., $^{14}N_2$, $^{15}N^{14}N$, and $^{15}N_2$). An isotopologue in which two or more rare isotopes are present in close proximity (isotopic "clumps") is called a multiply-substituted isotopologue or clumped isotope (e.g., $^{15}N_2$). The hydrocarbon isotopologues involve hydrocarbon compounds that have natural isotopes of $^{12}C$, $^{13}C$, $^1H$, or H (i.e., deuterium or D). $^{12}C$ represents about 98.93 mole percent (mol. %) of the total carbon on Earth, while $^{13}C$ forms the remaining 1.07 mol. %. Similarly, the isotopic abundance of $^1H$ on earth is 99.985 mol. % while D has an abundance of 0.015 mol. %. Common volatile hydrocarbons have large numbers of isotopologues even considering only the stable isotopes (e.g., methane has 10; ethane has 36; propane has 216). Common isotopologues of methane for example include $^{13}C^1H_3D$ or $^{12}C^1H_4$. In addition to the number of rare isotopes, the distribution of isotopes in the molecule can also provide information. For example, in a linear hydrocarbon compound with three carbon atoms, the rare isotope can take either a central or terminal (end of the molecule) position. Similarly, rare isotopes of hydrogen can occupy different positions. As the size of the hydrocarbon compound increases, the number of positions that these rare isotopes can be situated increases. This effect is called the position specific isotope signature or effect, or isotopomer geochemistry.

The multiply substituted isotopologue and the position specific isotope signature of any molecule are a function of (i) temperature-independent randomly populated processes (e.g., stochastic distribution) and (ii) other non-random mass fractionating processes. The stochastic distribution of any set of isotopologues can be determined from the bulk isotope signatures of the species from which it derives. For example, determining the stochastic distribution of isotopologues for methane involves knowledge of the $^{13}C$ and D signatures of methane. At equilibrium, a non-stochastic distribution may result from thermodynamic differences between the different isotopologues. Under non-equilibrium conditions, the non-random processes may be temperature-time dependent isotopic exchange reactions in some hydrocarbons. For example, multiply substituted isotopologue signatures in methane appear to provide equilibrium gas generation temperatures See, e.g., Stolper et al., Formation temperatures of thermogenic and biogenic methane, Science, 344, p. 1500-1503 (2014). Additional equilibrium or non-equilibrium kinetic isotope exchange processes may also influence the signatures in some hydrocarbon species. These processes may include, but are not limited to, biodegradation, secondary thermal cracking of hydrocarbons, thermochemical oxidation or reduction reactions, mixing or diffusion, physical processes such as sorption or desorption, or transport processes such as diffusion and advection. These processes may differ in their relative magnitude of the impact on the multiply substituted isotopologue and/or position specific isotope signatures. These processes result in changes in the concentrations and isotopic signatures of non-hydrocarbon compounds. By measuring the clumped and position specific isotope signatures of multiple hydrocarbon compounds that may be sensitive to different parameters, and through the integration of this information with other complimentary geochemical systems (such as, the noble gases that record physical processes; such as, diffusion, advection, and mixing processes amongst other things), one can determine the processes controlling these signatures and quantify the extent of this effect on the sample. Such information can then be used to quantify gas production from different sources of gas (e.g., sorbed, free gas, matrix gas, fracture gas) and determine the origin of stray gases in the immediate vicinity of a producing well. In addition, the introduction of a geochemical spike with a very exotic clumped isotope signature can be used to more rapidly detect leakage to these locations. Various aspects of the present techniques are described further in FIGS. 1 to 3.

Figure 1B:
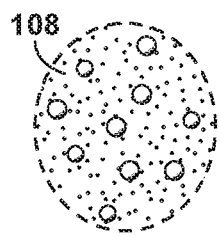
FIG. 1B is an expanded view illustrating free gases in the producing interval of FIG. 1A.
Figure 1C:
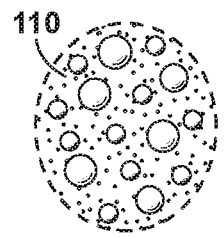
FIG. 1C is an expanded view illustrating gases that are sorbed to surfaces in the matrix of the producing interval of FIG. 1A.

FIG. 1A is a side elevational diagram 100 of the production of hydrocarbons in conventional or unconventional reservoirs, which is located below the surface 101. In this diagram 100, different sources of hydrocarbon fluids, flow by arrows 130, 132, 134, 136 and 138, are shown and produced in the well bore 102 to the surface and pipelines 103. These sources of hydrocarbons include hydrocarbons that reach the well bore through artificially induced fractures 107 in the producing strata or interval 104, or through fractures that extend into a different hydrocarbon bearing interval or strata 105. Gases may initially be present as a free gas phase in the producing interval, as shown in the expanded area 108 illustrated in FIG. 1B, or may be initially sorbed to surfaces in the matrix, as shown by expanded area 110 illustrated in FIG. 1C, until conditions change and they are liberated. Gas production may be dominated by flow from this matrix in the expanded areas 108 and 110, or may be dominated by from flow from fractures 107. Hydrocarbons may also leak from the producing well bore 102 into the well annulus 114. Understanding the source and flow of hydrocarbons is useful to prevent movement towards aquifers, such as aquifer 116, which may be a thousand feet or more from the producing interval 104.

Understanding the penetration depth and effectiveness of fractures propagated during fracking into tight oil and gas reservoirs may provide needed information that may be utilized to enhance hydrocarbon production. For example, some fractures may penetrate too far, and thereby breach the sealing horizons and penetrate into hydrocarbon-poor, water-rich units, and/or penetrate into different hydrocarbon-rich units. These fractures may be detected in produced fluids by a shift in the clumped isotope, position-specific, and/or inert gas/isotope signature due to mixing with fluids outside the principal reservoir. Such breaching may reduce production efficiency and could even lead to contamination of nearby intervals. The present techniques provide a mechanism for early recognition and monitoring of the extent of seal breach thereby allowing for optimized fracking operations. Even if a sealing unit is not breached, if enough differences exist in signatures throughout the target reservoir, a shift in signatures for produced fluids post-fracking may provide a mechanism to monitor and optimize fracture penetration as well as modeling reservoir drainage. Applications related to the penetration or breaching of seals or baffles may also enhance production efficiency and monitoring of high permeability (conventional) reservoirs.

Figure 2:
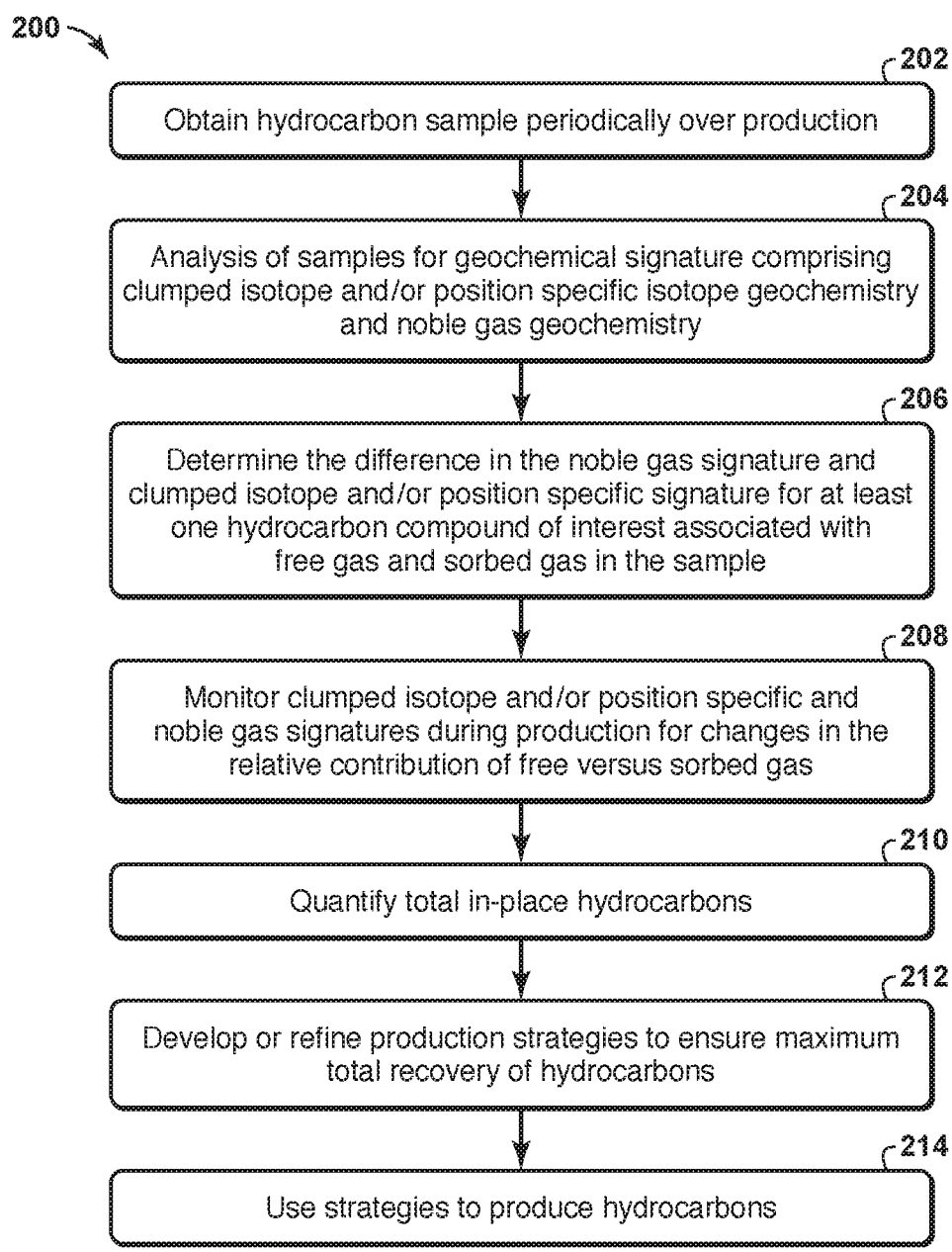
FIG. 2 is a flow diagram of an exemplary method to identify and quantify relative contributions of free gas and sorbed gas in the production stream from measured multiply substituted isotopologue or position specific isotope signatures to quantify total hydrocarbons in place and develop optimal depletion strategies for the production of hydrocarbons in accordance with an exemplary embodiment of the present techniques.

FIG. 2 is a flow diagram 200 of an exemplary method to identify and quantify relative contributions of free gas and sorbed gas in the production stream to quantify total hydrocarbons in place and develop optimal depletion strategies for the production of hydrocarbons in accordance with an exemplary embodiment of the present techniques. In this diagram 200, the method may be used to convert measured multiply substituted isotopologue or position specific isotope signatures into a temperature or identify a kinetic isotope effect associated with desorption and integrate this with noble gas data that provides information on physical processes such as sorption/desorption to identify free and sorbed gas. Further, this method may be used to identify changes in the relative contributions of these different sources of gas over the course of production and a shift from, for example, free gas dominated production to sorbed gas dominated production as pressure decreases in the reservoir. That is, the method may determine relative contributions of free gas as compared to sorbed gas in production stream and changes during production.

The method begins at block 202. In block 202, samples of hydrocarbons are collected at different stages of production. The samples may be from a target subsurface interval and may include a specific production interval or region within the subsurface formation. The sample may be obtained during drilling operations or at a first period of time prior to the subsequent samples below. This sample can be in the form of oil and/or gas obtained from within the wellbore or during flowing of the well (e.g., the initial flowing of well). Alternatively, a gas sample could be collected from mud circulating in the well bore.

At block 204, analysis of samples for geochemical signature comprising clumped isotope and/or position specific isotope geochemistry and noble gas geochemistry. The sample(s) geochemical signature may include multiply substituted isotopologue and/or position specific isotope geochemistry information. If methane, the primary chemical component of natural gases, is used as an example, it is possible to investigate the potential of forming the clumped doubly substituted isotopologue $^{13}CH_3D$, and the doubly substituted isotopologue $^{12}CH_2D_2$. This analysis may also include a variety of geochemical signatures comprising bulk composition, isotopic signatures of groups of elements, such as, the noble gases, molecular geochemistry, which may be used to provide additional information, such as, mass of water that has interacted with the fluid or to identify processes, such as mixing. The sample may be analyzed for its multiply substituted isotopologue and or isotope position specific signature. The measurement of the absolute abundance of isotopologues or position of interest for any given hydrocarbon involves knowledge of the molecular mass or absorption spectra at which they are present, and hence involves knowledge of the actual identity of each possible isotopologue for that species. Measurement of the abundance of each isotopologue or fragment can be conducted using multiple techniques, such as, mass spectrometry and/or laser-based spectroscopy. This analysis may also comprise noble gas analysis.

Then, at block 206, the difference in the noble gas signature and clumped isotope and/or position specific signature for at least one hydrocarbon compound of interest associated with free gas and sorbed gas in the sample is determined. The multiply substituted isotopologue and/or position specific isotope signature of at least one hydrocarbon compound of interest and/or noble gas signature of the sample is interpreted in the context of that likely representative of free gas or sorbed gas dominated. This can be done through comparison of the sample data with that obtained by experiment where a signature of sorbed gas is initially constrained. This can be done, for example, by taking a gas mixture containing hydrocarbons and other compounds and introducing it in to a sample vessel containing a solid that has a surface that promotes sorption and increasing the pressure in the sample container. Aliquots of the sample are then analyzed as the pressure is decreased to determine the fingerprint associated with the desorption process in the clumped isotopes/position specific effect signatures and the signatures of other compounds such as the noble gases. For example, it has been shown that heavy noble gases such as krypton and xenon have an affinity for organic rich sediments, and are thought to sorb to the surface of these sediments. See, e.g., Torgersen T. and Kennedy B. M. (1999) Air-Xe enrichments in Elk Hills oil field gases: Role of water in migration and storage. *Earth Planet. Sci. Lett.* 167, pp. 239-253. It is therefore expected that free gases may be depleted in these heavy noble gases, and that the concentration of krypton and xenon will increase with increasing contribution of sorbed gas to the produced gas over time. For example, the method may include monitoring the krypton to argon ratio and xenon to argon ratio during production and alter production strategies and flow techniques when these changes in ratios are observed in order to maximize total recovery.

Further, the method may involve converting each of the clumped isotope and/or position specific effect geochemistry to a sorption dependent fractionation factor for each of the hydrocarbon samples and then comparing the sorption dependent fractionation factor for the different hydrocarbon samples.

In block 208, the clumped isotope and/or position specific and noble gas signatures are monitored during production for changes in the relative contribution of free versus sorbed gas. The produced gas samples are routinely analyzed over production timescales to monitor changes in the relative contributions of free gas versus sorbed gas and how this changes as a function of total gas produced or other variables such as reservoir pressure.

At block 210, the total in-place hydrocarbons are quantified. That is, the relative contributions of free gas versus sorbed gas determined at different stages of production in block 208 as a function of total gas produced are used to calculate the total in-place sorbed hydrocarbon volume and total in-place free gas hydrocarbon volume.

Then, in block 212, production strategies may be made or refined to ensure maximum total recovery of hydrocarbons. That is, the information is used to develop or refine production strategies for any given well in the same or analogous hydrocarbon system when some estimate of reservoir pressure or other controlling variable is known or can be predicted. In this manner, it may be possible to access a great volume of hydrocarbons by, for example, more slowly decreasing reservoir pressure to access a greater proportion of free gas relative to sorbed gas or vice versa.

At block 214, the information or strategies are used to produce hydrocarbons. That is, based on the comparison, drilling of a well may be performed to provide access to the hydrocarbon accumulation. Further, the production may include installing or modifying a production facility for the production of hydrocarbons from the production intervals that provide access to the hydrocarbons in the subsurface formation. The production facility may include one or more units to process and manage the flow of production fluids, such as hydrocarbons and/or water, from the formation. To access the production intervals, the production facility may be coupled to a tree and various control valves via a control umbilical, production tubing for passing fluids from the tree to the production facility, control tubing for hydraulic or electrical devices, and a control cable for communicating with other devices within the wellbore. The strategy may adjust the well locations, fracture depths and patterns, etc.

Further, as another example, it is useful for reserves estimation and well performance prediction to understand the physical origin of hydrocarbons. Both matrix and fracture fluids can contribute to production, as can sorbed and free fluids. Production strategies can differ significantly for these different fluids and it is therefore useful to be able to recognize and monitor the contributions of each. Clumped isotope and position-specific isotope signatures can be affected by sorption and may therefore reflect contribution of adsorbed versus free gas.

This combined geochemical signature comprising noble gases and clumped isotopes can also be used to provide an enhancement in the production and exploration of hydrocarbons by allowing discrimination between fracture and matrix-dominated flow regimes. In particular, the method may be utilized to enhance production operations. Further, the integration of this information with seismic data with gravity, magnetics, and acoustic data from other measurements, subsurface model or other information may provide additional insights to enhance the operations.

Figure 3:
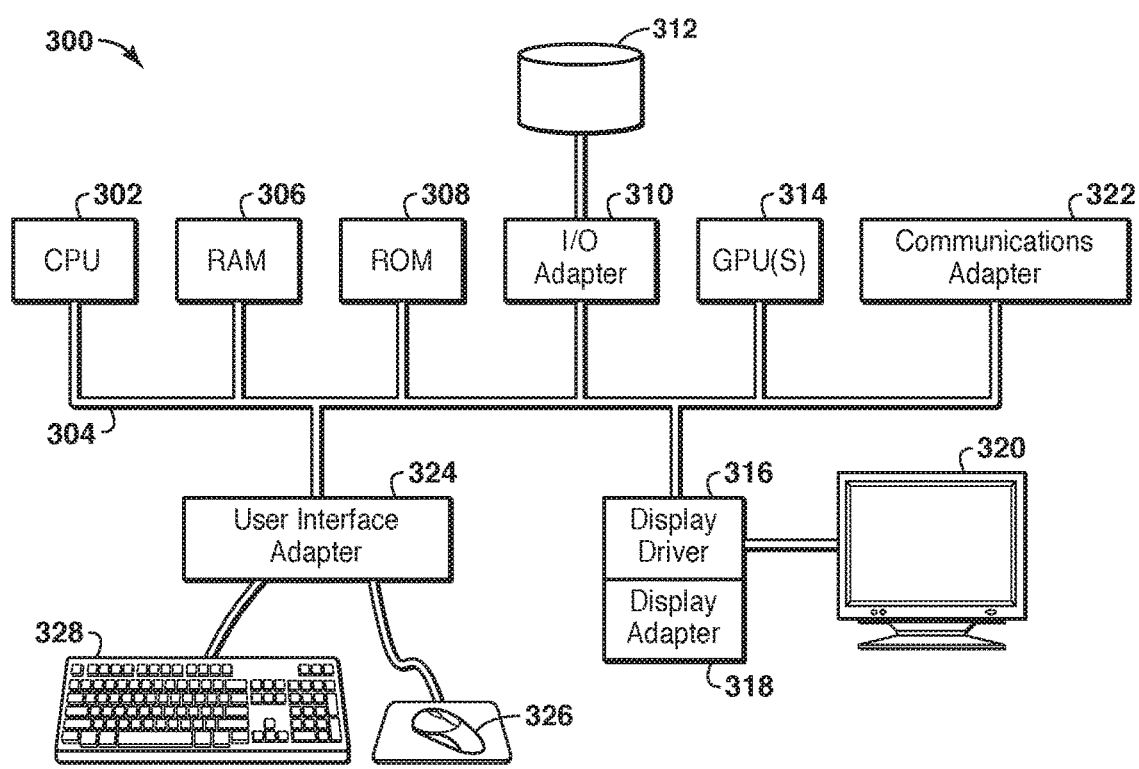
FIG. 3 is a block diagram of a computer system in accordance with an exemplary embodiment of the present techniques.

FIG. 3 is a block diagram of a computer system 300 in accordance with an exemplary embodiment of the present techniques. A central processing unit (CPU) 302 is coupled to system bus 304. The CPU 302 may be any general-purpose CPU, although other types of architectures of CPU 302 (or other components of exemplary system 300) may be used as long as CPU 302 (and other components of system 300) supports the inventive operations as described herein. The CPU 302 may execute the various logical instructions according to various exemplary embodiments. For example, the CPU 302 may execute machine-level instructions for performing processing according to the operational flow described above.

The computer system 300 may also include computer components such as a random access memory (RAM) 306, which may be SRAM, DRAM, SDRAM, or the like. The computer system 300 may also include read-only memory (ROM) 308, which may be PROM, EPROM, EEPROM, or the like. RAM 306 and ROM 308 hold user and system data and programs, as is known in the art. The computer system 300 may also include an input/output (I/O) adapter 310, GPU(s) 314, a communications adapter 322, a user interface adapter 324, and a display adapter 318. The I/O adapter 310, the user interface adapter 324, and/or communications adapter 322 may, in certain embodiments, enable a user to interact with computer system 300 in order to input information.

The I/O adapter 310 preferably connects a storage device(s) 312, such as one or more of hard drive, compact disc (CD) drive, floppy disk drive, tape drive, etc. to computer system 300. The storage device(s) may be used when RAM 306 is insufficient for the memory requirements associated with storing data for operations of embodiments of the present techniques. The data storage of the computer system 300 may be used for storing information and/or other data used or generated as disclosed herein. The communications adapter 322 may couple the computer system 300 to a network (not shown), which may enable information to be input to and/or output from system 300 via the network (for example, the Internet or other wide-area network, a local-area network, a public or private switched telephony network, a wireless network, any combination of the foregoing). User interface adapter 324 couples user input devices, such as a keyboard 328, a pointing device 326, and the like, to computer system 300. The display adapter 318 is driven by the CPU 302 to control, through a display driver 316, the display on a display device 320. Information and/or representations pertaining to a portion of a supply chain design or a shipping simulation, such as displaying data corresponding to a physical or financial property of interest, may thereby be displayed, according to certain exemplary embodiments.

The architecture of system 300 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

As an example, machine-readable logic or code may be used or executed with a computing system, such as computing system 300 of FIG. 3. The code or a set of instructions is provided enhancing hydrocarbon production, which may include analyzing hydrocarbon samples for geochemical signature comprising clumped isotope and/or position specific isotope geochemistry and noble gas geochemistry. When executed or applied with a computer system, such as computer system 300, code is configured to obtain hydrocarbon sample data for each of a plurality of hydrocarbon samples from a target subsurface interval; analyze the hydrocarbon sample data for each of the plurality of hydrocarbon samples for geochemical signature comprising clumped isotope and/or position specific isotope geochemistry for at least one hydrocarbon compound of interest associated with free gas and sorbed gas; converting each of the clumped isotope and/or position specific effect geochemistry to a sorption dependent fractionation factor for each of the plurality of hydrocarbon samples; comparing the sorption dependent fractionation factor of at least two of the plurality of hydrocarbon samples; determining whether the at least one hydrocarbon compound of interest associated with free gas and sorbed gas has originated from the target interval or from a different interval; and adjust a recovery strategy based on the determination.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

What is claimed is:

1. A method for enhancing hydrocarbon production comprising:
   obtaining a plurality of samples comprising hydrocarbons from a target subsurface interval of a reservoir;
   analyzing each of the plurality of samples for a geochemical signature comprising a clumped isotope signature and/or a position specific isotope signature for at least one hydrocarbon compound of interest associated with free gas and sorbed gas in the sample;
   converting each of the clumped isotope signature and/or position specific isotope signature for the hydrocarbon compound of interest to a sorption dependent fractionation factor for each of the plurality of samples, wherein the sorption dependent fractionation factor describes the difference in the clumped isotope signature and/or position specific isotope signature for the hydrocarbon compound of interest associated with free gas in the sample and the clumped isotope signature and/or position specific isotope signature for the hydrocarbon compound of interest associated with the sorbed gas in the sample;
   comparing the sorption dependent fractionation factor of at least two of the plurality of samples;
   determining whether the at least one hydrocarbon compound of interest associated with free gas and sorbed gas in the sample has originated from the target interval or from a different interval; and
   adjusting a recovery strategy for the reservoir based on the determination.

2. The method of claim 1, wherein analyzing each of the plurality of samples for the geochemical signature further comprises determining noble gas signature.

3. The method of claim 2, further comprising determining differences between the noble gas signatures for at least two of the plurality of samples.

4. The method of claim 1, wherein the determination involves analyzing each of the at least two of the plurality of samples to identify a source contribution for each of the at least two of the plurality of samples.

5. The method of claim 1, comprising monitoring the geochemical signature of the plurality of samples during production for changes in the source contribution for each of the plurality of samples.

6. The method of claim 1, further comprising quantifying total in-place hydrocarbons from the source contribution of the respective sample.

7. A system for enhancing hydrocarbon production, comprising:
   a processor;
   an input device in communication with the processor and configured to receive input data associated with a subsurface formation;
   memory in communication with the processor, the memory having a set of instructions, wherein the set of instructions, when executed, are configured to:
      obtain sample data for each of a plurality of samples from a target subsurface interval;
      analyze the sample data for each of the plurality of samples for a geochemical signature comprising a clumped isotope signature and/or a position specific isotope signature for at least one hydrocarbon compound of interest associated with free gas and sorbed gas in the sample;
      converting each of the clumped isotope signature and/or position specific isotope signature for the hydrocarbon compound of interest to a sorption dependent fractionation factor for each of the plurality of samples, wherein the sorption dependent fractionation factor describes the difference in the clumped isotope signature and/or position specific isotope signature for the hydrocarbon compound of interest associated with free gas in the sample and the clumped isotope signature and/or position specific isotope signature for the hydrocarbon compound of interest associated with the sorbed gas in the sample;
      comparing the sorption dependent fractionation factor of at least two of the plurality of samples;
      determining whether the at least one hydrocarbon compound of interest associated with free gas and sorbed gas in the sample has originated from the target interval or from a different interval; and
      adjust a recovery strategy based on the determination; and
   an output device that outputs the adjusted recovery strategy.

8. The system of claim 7, wherein the set of instructions are further configured to:
   determine noble gas geochemistry from the plurality of samples.

9. The system of claim 7, wherein the set of instructions are further configured to analyze each of the at least two of the plurality of samples to identify a source contribution for each of the at least two of the plurality of samples.

10. The system of claim 7, wherein the set of instructions are further configured to monitoring the geochemical signature of the plurality of samples during production for changes in the source contribution for each of the plurality of samples.

11. The system of claim 7, wherein the set of instructions are further configured to quantify total in-place hydrocarbons from the source contribution of the respective sample.

* * * * *